United States Patent [19]

Steffan

[11] Patent Number: 5,719,285
[45] Date of Patent: Feb. 17, 1998

[54] PROCESS FOR THE PREPARATION OF POLYCHLOROPYRIMIDINES

[75] Inventor: Guido Steffan, Odenthal, Germany

[73] Assignee: Bayer Aktiengesellschaft, Leverkusen, Germany

[21] Appl. No.: 514,278

[22] Filed: Aug. 11, 1995

[30] Foreign Application Priority Data

Aug. 19, 1994 [DE] Germany ............... 44 29 466.2

[51] Int. Cl.$^6$ ............................................. C07D 239/30
[52] U.S. Cl. ................ 544/334; 544/299; 544/319
[58] Field of Search ................... 544/319, 334, 544/299

[56] References Cited

U.S. PATENT DOCUMENTS 3,714,164  1/1973  Steffan .................... 544/334

FOREIGN PATENT DOCUMENTS 0101561  12/1984  European Pat. Off. .
1933784   1/1971  Germany .

OTHER PUBLICATIONS

A.E.A. Porter, in: "Comprehensive Organic Chemistry",vol. 4, pp. 119 –120, P.G. Sammes ed., Pergamon Press Ltd., New York, (1979).

D.J. Brown, in: "Comprehensive Heterocyclic Chemistry", A.R. Katritzky, et al. ed., vol. 3, Part 2B, p. 89, Pergamon Press Ltd., New York, (1984).

D.J. Brown, et al., in "The Chemistry of Heterocyclic Compounds", E.C. Taylor ed., vol. 52, pp. 329–339 , J. Wiley & Sons, New York, (1994).

G.W. Kenner, et al., J. Chem. Soc., London, pp. 574–575 (1943).

R. Hall, J. Chem. Soc., London, P. 2214 (1951).

C. Hennart et al., Bull. Chim. Soc., France, pp. 741–742 (1959).

V.A. Zasosov, Khim.-Pharm. Zhurnal, vol. 8, No. 12 pp. 741–744 (1974).

*Primary Examiner*—Yogendra N. Gupta
*Attorney, Agent, or Firm*—Sprung Kramer Schaffer & Briscoe

[57] ABSTRACT

Polychloropyrimidines, in particular 4,6-dichloropyrimidine and 2,4,6-trichloropyrimidine, are obtained in a particularly advantageous manner from polyhydroxypyrimidines or tautomeric keto compounds thereof and excess phosphorus oxychloride in the presence of a tertiary amine if, in this reaction, a) 0.75 to 1.5 mol of phosphorus trichloride and 0.7 to 1.4 mol of chlorine per equivalent of hydroxyl groups to be replaced by chlorine are added such that an excess of phosphorus trichloride over chlorine is always present and b) phosphorus oxychloride and the polychloropyrimidine prepared are distilled off successively over a column under reduced pressure, or steps a) and b) are carried out in the reverse sequence, phosphorus trichloride also being distilled off before the phosphorus oxychloride in the case of b) after a) and phosphorus oxychloride which has formed again after step a) has been carried out being distilled off in the case of a) after b), and c) a strong base is added to the distillation residue which is then present, and the tertiary amine employed is recovered from this mixture by d) separating off the upper phase and e) purifying it by distillation, or carrying out steps d) and e) in the reverse sequence.

14 Claims, No Drawings

PROCESS FOR THE PREPARATION OF POLYCHLOROPYRIMIDINES

The present invention relates to an improved process for the preparation of polychloropyrimidines, in particular 4,6-dichloropyrimidine, from 4,6-dihydroxypyrimidine and 2,4,6-trichloropyrimidine from barbituric acid.

Polychloropyrimidines are intermediate products for the preparation of plant protection agents and dyestuffs.

In the known processes for the preparation of 4,6-dichloropyrimidine, phosphorus oxychloride and dimethylaniline or pyridine are added to 4,6-dihydroxypyrimidine (cf. J. Chem. Soc. 1943, 574; J. Chem. Soc. 1951, 2214; Bull. Soc. Chim. France 1959, 741 and Khim.-Pharm. Zhurnal 8 (12), 28 (1974)—English translation page 741).

For working up in this process, excess phosphorus oxychloride is first stripped off and the residue is then either discharged onto ice and the product is obtained by extraction and crystallization, or subjected to sublimation, in which the product is obtained as the sublimate. The disadvantage of this process is that dimethylaniline or pyridine are employed in large mounts, but can be recovered and re-used only with considerable effort. Furthermore, the yields (not more than 81.1% of theory) are still in need of improvement. Finally, aqueous working up is very expensive because of the disposal of the waste waters formed and the handling of extraction agents. Working up by sublimation is also very expensive on an industrial scale, for example in respect of the apparatuses to be employed and the industrial hygiene requirements, in order to remove the product from the sublimator.

Our own attempts to design the known processes more advantageously by using smaller amounts of dimethylaniline failed because the yield of 4,6-dichloropyrimidine is then severely reduced and the formation of high-boiling constituents and resins increases greatly (cf. Example 7).

A process has now been found for the preparation of polychloropyrimidines by reaction of polyhydroxypyrimidines or tautomeric keto compounds thereof with excess phosphorus oxychloride in the presence of a tertiary amine, which is characterized in that, in this reaction, a) 0.75 to 1.5 mol of phosphorus trichloride and 0.7 to 1.4 mol of chlorine per equivalent of hydroxyl groups to be replaced by chlorine are added such that an excess of phosphorus trichloride over chlorine is always present and b) phosphorus oxychloride and the polychloropyrimidine prepared are distilled off successively over a column under reduced pressure, or steps a) and b) are carried out in the reverse sequence, phosphorus trichloride also being distilled off before the phosphorus oxychloride in the case of b) after a) and phosphorus oxychloride which has formed again after step a) has been carried out being distilled off in the case of a) after b), and c) a strong base is added to the distillation residue which is then present, and the tertiary amine employed is recovered from this mixture by d) separating off the upper phase and e) purifying it by distillation, or carrying out steps, d) and e) in the reverse sequence.

Preferably, 4,6-dihydroxypyrimidine or barbituric acid (which is the keto form of 2,4,6-trihydroxypyrimidine) is employed in the process according to the invention and 4,6-dichloro- or 2,4,6-trichloropyrimidine is prepared.

4,6-Dihydroxypyrimidine is a known compound which is accessible, for example, from malonic acid diamide and ethyl formate (J. Chem. Soc. 1951, 2214). Barbituric acid, phosphorus oxychloride, phosphorus trichloride and chlorine are commercially obtainable.

2.5 to 12 mol of phosphorus oxychloride, for example, can be employed per mole of polyhydroxypyrimidine. This amount is preferably 3.5 to 5 mol when 4,6-dihydroxypyrimidine is employed and 4.5 to 10 mol when barbituric acid is employed.

Suitable tertiary amines are, for example, alkylated pyridines, alkylated imidazoles, alkylated indoles, N-dialkylated anilines and tertiary N-alkylamines. Alkylated pyridines, alkylated imidazoles and alkylated indoles are preferred. 2-Methyl-5-ethyl-pyridine, 1,2-dimethylimidazole and 2,3,3-trimethylindolenine are particularly preferred.

The tertiary amine can be employed, for example, in amounts of 1 to 5 mol per mole of polyhydroxypyrimidine. This amount is preferably 1.8 to 2.2 mol when 4,6-dihydroxypyrimidine is employed and 2.7 to 3.5 mol when barbituric acid is employed.

Temperatures in the range from 0° to 120° C., for example, are suitable for the reaction of polyhydroxypyrimidines with phosphorus oxychloride in the presence of tertiary amines. Temperatures of 20° to 100° C. are preferred. A procedure can be followed here, for example, in which the phosphorus oxychloride and the polyhydroxypyrimidine are initially introduced into the reaction vessel and the tertiary amine is metered in. It is advantageous with this procedure to start the metering at a low temperature, for example at 0° to 30° C., and to end the metering at a higher temperature, for example at 60° to 95° C., and to subsequently stir the mixture for a further 1 to 5 hours at higher temperature, for example at 80° to 105° C.

A procedure can also be followed in which the phosphorus oxychloride and the tertiary amine are initially introduced into the reaction vessel and the polyhydroxypyrimidine is metered in. It is advantageous here to carry out the metering at 80° to 105° C. and to subsequently stir the mixture for a further 1 to 5 hours at this temperature.

Other procedures and other temperatures in the range from 0° to 120° C. are also possible.

Thereafter, according to stage a), the abovementioned amounts of phosphorus trichloride and chlorine are added to the reaction mixture such that an excess of phosphorus trichloride over chlorine is always present in the reaction mixture. The excess is advantageously chosen such that 0.3 to 5% by weight, preferably 0.5 to 2% by weight, of free phosphorus trichloride is always present in the reaction mixture. A procedure can be followed here in which phosphorus trichloride and chlorine are metered in uniformly with a brief initial addition of phosphorus trichloride. The phosphorus trichloride and chlorine can be added, for example, at 60° to 120° C. When the addition of phosphorus trichloride and chlorine has ended, it is advantageous subsequently to stir the mixture at 60° to 105° C. for some time, for example 10 minutes to 3 hours.

For working up the reaction mixture according to stage b), it is first subjected to fractional distillation over a column under reduced pressure. The pressure can initially be, for example, 500 to 50 mbar. The column can have, for example, 5 to 20 theoretical plates. The column can be operated, for example, with a reflux ratio of 0.8 to 5:1. The phosphorus trichloride still present, which is usually only a small amount, is first distilled off. Phosphorus oxychloride follows as the next fraction and, like the phosphorus trichloride distilled off, can be re-used. It is then advantageous to adjust the pressure, for example in the range from 100 to 5 mbar, and to distill off the polychloropyrimidine prepared at bottom temperatures of up to 160° to 200° C. This product can be collected in one fraction.

If particularly pure polychloropyrimidine is to be obtained, it is advantageous first to collect a main fraction which comprises polychloropyrimidine in a purity of more than 97%. As the condensing distillate starts to acquire a slightly yellow colouration, after-runnings which comprise polychloropyrimidine in a purity of more than 80% and amounts to about 5 to 10% by weight of the main fraction can then also be collected. These after-runnings can be recycled into the corresponding distillation during working up of the next batch.

Polychloropyrimidines, in particular 4,6-dichloropyrimidine, can be obtained in yields of about 80 to virtually 100% by the process according to the invention, inter alia independently of the tertiary amine employed. With the tertiary amines which are preferably to be employed, the yields are in the range from 95 to virtually 100%.

Stages a) and b) can also be carried out in the reverse sequence. If the sequence b)→a) is followed, phosphorus oxychloride which has formed again after stage a) is then to be distilled off.

With the sequence a)→b), a polychloropyrimidine which comprises traces of phosphorus oxychloride is obtained. With the reverse sequence, that is to say b)→a), a polychloropyrimidine which comprises traces of the tertiary amine is obtained. The sequences possible here will first be chosen such that a polychloropyrimidine of which the impurities cause the least trouble during further processing is obtained.

Polychloropyrimidines which comprise practically no more impurities can be obtained if the polychloropyrimidine distilled off in stage b) is subjected to a second distillation or the distillation for removal of the polychloropyrimidine is carried out as rectification.

According to stage c), a strong base is now added to the distillation residue which remains after the polychloropyrimidine has been separated off and comprises, as essential constituent, the hydrochloride of the tertiary amine employed. Suitable bases are, for example, concentrated aqueous solutions of alkali metal hydroxides. It is possible to employ, for example, 1 to 2 mol, for example, of 35 to 55% strength by weight aqueous potassium hydroxide solutions or sodium hydroxide solutions per mole of tertiary amine employed. The strong base is preferably added to the distillation residue at those temperatures at which the latter is stirrable—although only with difficulty under certain circumstances. Temperatures of 60° to 100° C. are often suitable. The strong base can be added relatively slowly, for example in the course of ½ to 5 hours, and while stirring thoroughly.

The upper phase is then separated off (stage d)).

The upper phase is now distilled again under reduced pressure in accordance with stage e). The pressure can be, for example, 100 to 10 mbar. During the distillation, the mixture is preferably stirred and the bottom temperature is raised to for example, 150° to 200° C. until the end of the distillation.

A 2-phase distillate is obtained by this distillation. The lower, aqueous phase in general comprises only little tertiary amine, for example less than 1% by weight of that employed. The upper, organic phase comprises the tertiary amine recovered, usually more than 90% by weight of the mount employed, in a purity of more than 95%. After traces of water have been stripped off, it can be re-used for the reaction of polyhydroxypyrimidines with phosphorus oxychloride.

The distillation leaves behind a brown salt mass which can be removed from the distillation vessel by dissolving in water.

Stages d) and e) can also be carried out in the reverse sequence.

With the sequence d)→e), it is advantageous to introduce larger amounts of water or to use a more dilute strong base in order to obtain two liquid phases which are free from solids and can easily be separated from one another. Although the mount of waste water obtained is thereby increased, simple apparatuses can be used.

With the reverse sequence, that is to say e)→d), the strong base can also be used in concentrated form, for example as a 50 to 80% strength by weight aqueous potassium hydroxide or sodium hydroxide solution. Less waste water is formed with this procedure, but it requires more complicated apparatus, for example paddle driers.

The process according to the invention has a number of advantages which render it particularly suitable for use on an industrial scale. Thus, the tertiary amine employed can be recovered and used again. The yields of polychloropyrimidines, in particular 4,6-dichloropyrimidine, are virtually 100% of theory if certain tertiary amines are employed, and are otherwise the same or even better than with known processes. As a result of the distillative working up which is now possible, very much smaller amounts of waste products which are much easier to dispose of are formed. Sublimation apparatuses and extraction agents do not have to be handled. Not only the phosphorus oxychloride employed in excess but also the phosphorus oxychloride newly formed from phosphorus trichloride in the process according to the invention is obtained in such a pure form that it can be further used as desired.

EXAMPLES

Example 1

2680 g of phosphorus oxychloride and 460 g of 4,6-dihydroxypyrimidine (98% pure) were mixed, and 980 g of 2-methyl-5-ethyl-pyridine were metered in, starting at room temperature, in the course of 90 minutes with stirring. During this operation, the temperature was limited to a maximum of 80° C. by cooling. The mixture was then subsequently stirred at 90° C. for 1 hour and at 100° C. for 1 hour. 1105 g of phosphorus trichloride and 570 g of chlorine were now simultaneously metered in at 100° C. in the course of 1 hour such that 25 ml of phosphorus trichloride were always present in the reaction batch in excess over the chlorine passed in. The mixture was subsequently stirred at 100° C. for 30 minutes, and first a small amount of phosphorus trichloride and then 3835 g of phosphorus oxychloride were distilled off up to a bottom temperature of 130° C. over a column with 20 theoretical plates and a reflux ratio rising from 1:1 to 3:1 under 100 mbar. The 4,6-dichloropyrimidine prepared was then distilled off over a short column with 3 theoretical plates under 20 mbar up to a bottom temperature of 175° C., initially 553 g of main running (purity 98.1%; yield 91% of theory) and then, as distillation of the amine hydrochloride starts (slightly yellowish syrupy condensate), 41 g of after-runnings (purity 88%; yield 6% of theory) being obtained. The total yield of 4,6-dichloropyrimidine was accordingly 97% of theory.

Thereafter, 800 g of 50% strength aqueous sodium hydroxide solution were added to the viscous distillation residue at 90° C. in the course of 2 hours, while stirring thoroughly. The mixture was then distilled to dryness under 50 mbar at a bottom temperature of 170° C., while stirring vigorously. The distillate was composed of 492 g of an aqueous lower phase comprising 0.5% by weight of the 2-methyl-5-ethyl-pyridine employed and 932 g of an organic upper phase composed of 2-methyl-5-ethyl-pyridine to the extent of 98.8% by weight, which corresponds to 94% by weight of the amount employed. The pulverulent salt-like distillation residue dissolved almost completely in water.

Example 2

2680 g of phosphorus oxychloride were initially introduced into the reaction vessel and 980 g of 2-methyl-5-ethyl-pyridine were added, while cooling. 460 g of 4,6-dihydroxypyrimidine were then metered in over a period of 1 hour. Further reaction and working up were carried out as described in Example 1.

4,6-Dichloropyrimidine was obtained in a yield of virtually 100% and 88% by weight of the amount of amine employed was recovered.

Examples 3 to 6

The procedure was as in Example 1, but a different tertiary amine was employed in each case and several batches were carried out in each case.

Example 3

2,3,3-Trimethylindolenine, yield of 4,6-dichloropyrimidine: 98 to 100% of theory.

Example 4

1,2-Dimethylimidazole, yield of 4,6-dichloropyrimidine: 97 to 99% of theory.

Example 5

N-dimethylaniline, yield of 4,6-dichloropyrimidine: 78 to 88% of theory.

Example 6

Tri-n-butylamine, yield of 4,6-dichloropyrimidine: 75 to 85% of theory.

Example 7: (for comparison)

460 g of phosphorus oxychloride and 62 g of N,N-dimethylaniline were mixed and 116 g of 4,6-dihydroxypyrimidine (98% pure) were metered into the mixture with a screw at 100° C. in the course of 5 hours. Thereafter, the reaction mixture was subsequently stirred at 106° to 128° C. for 8 hours. It was diluted with 300 g of chlorobenzene and discharged onto 1.2 kg of ice. The organic phase was separated off, washed twice with 100 ml of water each time and then subjected to fractional distillation. 85.7 g of 4,6-dichloropyrimidine (=58% of theory) are thus obtained.

Example 8

2680 g of phosphorus oxychloride were initially introduced into the reaction vessel and 980 g of 2-methyl-5-ethylpyridine were added, while cooling. 460 g of 4,6-dihydroxypyrimidine were then metered in such that the temperature did not rise above 40° C.

After an after-reaction at 40° to 45° C. for half an hour, first phosphorus oxychloride and then 4,6-dichloropyrimidine were distilled off as described in Example 1.

1390 g of phosphorus oxychloride and 595 g of 4,6-dichloropyrimidine (content 98.2%) were obtained, which corresponds to a yield of 98% of theory.

The distillation residue - essentially the dichlorophosphoric acid salt of methylethylpyridine—was reacted with 1200 g of phosphorus trichloride, 600 g of phosphorus oxychloride and 570 g of chlorine at a temperature rising from 80° to 100° C. Thereafter—as described in Example 1—first 100 g of phosphorus trichloride and then 1810 g of phosphorus oxychloride were obtained by distillation.

The viscous distillation residue was worked up as described in Example 1.

902 g of methyl-ethylpyridine were recovered (92% of the amount employed).

Example 9

128.0 g of barbituric acid were stirred with 700 g of phosphorus oxychloride. 242 g of 2-methyl-5-ethylpyridine were then added dropwise in the course of 1 hour such that the temperature did not rise above 55° C. The mixture was then subsequently stirred in each case for half an hour at 70°, 80° and 90° C., after which the barbituric acid had practically dissolved completely. After addition of 80 g of phosphorus trichloride, 411 g of phosphorus trichloride and 215 g of chlorine were metered in simultaneously at temperatures of 90° to 95° C. in the course of 2 hours. The mixture was then allowed to after-react under reflux at 100° C. for 30 minutes.

When the evolution of HCl had ended, a small mount of phosphorus trichloride was first distilled off under 100 mbar over a column with 20 theoretical plates and a reflux ratio rising from 1:1 to 3:1, and 1135 g of phosphorus oxychloride were then distilled off under 50 mbar, up to a bottom temperature of 135° C. Thereafter, 172 g of 2,4,6-trichloropyrimidine (98.1% pure) were obtained by distillation over a 5-plate column under 4 to 5 mbar and at a bottom temperature of between 96° and 140° C. and a top temperature of between 75° and 120° C., which corresponds to a yield of 96% of theory.

The viscous distillation residue (316 g) was worked up as described in Example 1. 226 g of methyl-ethylpyridine were recovered (93% of the amount employed).

What is claimed is:

1. A process for the preparation of a 4,6- or 2,4,6-polychloropyrimidine by reaction of a 4,6- or 2,4,6-polyhydroxypyrinidine or a tautomeric keto compound thereof with excess phosphorus oxychloride in the presence of a tertiary amine, in which reaction a) 0.75 to 1.5 mol of phosphorus trichloride and 0.7 to 1.4 mol of chlorine per equivalent of hydroxyl groups to be replaced by chlorine are added such that an excess of phosphorus trichloride over chlorine is always present and b) phosphorus oxychloride and fie polychloropyrimidine prepared are distilled off successively over a column under reduced pressure, and phosphorus trichloride also being distilled off before the phosphorus oxychloride, c) a strong base is added to the distillation residue which is then present, and the tertiary amine employed is recovered from this mixture by d) separating off the upper phase and e) purifying it by distillation.

2. The process of claim 1, in which steps a) and b) are carried out in the reverse sequence and phosphorus oxychloride which has formed again after step a) has been carried out being distilled off.

3. The process of claim 1, in which steps d) and e) are carried out in the reverse sequence.

4. The process of claim 1, in which 4,6-dihydroxypyrimidine or barbituric acid is set in and 4,6-dichloro- or 2,4,6-trichloropyrimidine is prepared.

5. The process of claim 1, in which 2.5 to 12 mol of phosphorus oxychloride are employed per mole of polyhydroxypyrimidine.

6. The process of claim 1, in which an alkylated pyridine, an alkylated imidazole, an alkylated indole, an N-dialkylated aniline or a tertiary N-alkylamine is employed as the tertiary amine in an amount of 1 to 5 mol per mole of polyhydroxypyrimidine.

7. The process of claim 1, in which the reaction of the polyhydroxypyrimidine with phosphorus oxychloride in the presence of a tertiary amine is carried out at 0° to 120° C. and phosphorus trichloride and chlorine are added at 60° to 105° C.

8. The process of claim 1, in which the phosphorus trichloride and phosphorus oxychloride are distilled off under a pressure of 500 to 50 mbar and the polychloropyrimidine is distilled off under pressures of 100 to 5 mbar and at a bottom temperature of up to 160° to 200° C.

9. The process of claim 1, in which the phosphorus oxychloride employed in excess and that newly formed are further used as desired after removal thereof.

10. The process of claim 1, in which the polychloropyrimidine is collected as the main fraction and as afterrunnings.

11. The process of claim 1, in which a concentrated aqueous solution of an alkali metal hydroxide is employed as the strong base in an mount of 1 to 2 mol per mole of tertiary amine employed.

12. The process of claim 1, in which the tertiary amine employed is distilled off under 100 to 10 mbar and at a bottom temperature of up to 150° to 200° C., and a lower, aqueous phase and an upper phase comprising the tertiary amine are obtained as the distillate.

13. The process of claim 2, in which 2.5 to 12 mol of phosphorus oxychloride are employed per mole of polyhydroxypyrimidine, an alkylated pyridine, an alkylated imidazole, an alkylated indole, an N-dialkylated aniline or a tertiary N-alkylamine is employed as the tertiary amine in an amount of 1 to 5 mol per mole of polyhydroxypyrimidine, the reaction of the polyhydroxypyrimidine with phosphorus oxychloride in the presence of a tertiary amine is carried out at 0° to 120° C. and phosphorus trichloride and chlorine are added at 60° to 105° C., the phosphorus trichloride and phosphorus oxychloride are distilled off under a pressure of 500 to 50 mbar and the polychloropyrimidine is distilled off under a pressure of 100 to 5 mbar and at a bottom temperature of up to 160° to 200° C., a concentrated aqueous solution of an alkali metal hydroxide is employed as the strong base in an amount of 1 to 2 mol per mole of tertiary amine employed and the tertiary amine employed is distilled off under 100 to 10 mbar and at a bottom temperature of up to 150° to 200° C., and a lower, aqueous phase and an upper phase comprising the tertiary amine are obtained as distillate.

14. The process of claim 3, in which 2.5 to 12 mol of phosphorus oxychloride are employed per mole of polyhydroxypyrimidine, an alkylated pyridine, an alkylated imidazole, an alkylated indole, an N-dialkylated aniline or a tertiary N-alkylamine is employed as the tertiary amine in an mount of 1 to 5 mol per mole of polyhydroxypyrimidine, the reaction of the polyhydroxy-pyrimidine with phosphorus oxychloride in the presence of a tertiary amine is carried out at 0° to 120° C. and phosphorus trichloride and chlorine are added at 60° to 105° C., the phosphorus trichloride and phosphorus oxychloride are distilled off under a pressure of 500 to 50 mbar and the polychloropyrimidine is distilled off under a pressure of 100 to 5 mbar and at a bottom temperature of up to 160° to 200° C., a concentrated aqueous solution of an alkali metal hydroxide is employed as the strong base in an amount of 1 to 2 mol per mole of tertiary amine employed and the tertiary amine employed is distilled off under 100 to 10 mbar and at a bottom temperature of up to 150° to 200° C., and a lower, aqueous phase and an upper phase comprising the tertiary amine are obtained as distillate.

* * * * *